United States Patent [19]

Ojo-Amaize

[11] Patent Number: 5,968,912
[45] Date of Patent: *Oct. 19, 1999

[54] METHODS FOR IMMUNOSUPPRESSING

[75] Inventor: Emmanuel A. Ojo-Amaize, Glendora, Calif.

[73] Assignee: Immune Modulation, Inc., Bloomington, Calif.

[ * ] Notice: This patent is subject to a terminal disclaimer.

[21] Appl. No.: 08/906,138

[22] Filed: Jul. 25, 1997

Related U.S. Application Data

[63] Continuation of application No. 08/688,002, Jul. 29, 1996, Pat. No. 5,747,474.

[51] Int. Cl.$^6$ .................................................. A61K 31/70
[52] U.S. Cl. ........................... 514/46; 514/47; 536/26.13; 536/27.62
[58] Field of Search .................... 514/46, 47; 536/26.13, 536/27.62

[56] References Cited

U.S. PATENT DOCUMENTS

| | | | |
|---|---|---|---|
| 4,309,419 | 1/1982 | Wolberg et al. | 514/43 |
| 4,369,181 | 1/1983 | Miller et al. | 514/46 |
| 4,861,873 | 8/1989 | Robins et al. | 536/26.13 |
| 4,873,227 | 10/1989 | Ikada et al. | 514/47 |
| 5,246,922 | 9/1993 | Kataoka et al. | 514/47 |
| 5,364,862 | 11/1994 | Spada et al. | 514/303 |
| 5,561,134 | 10/1996 | Spada et al. | 514/266 |
| 5,747,474 | 5/1998 | Ojo-Amaize et al. | 514/46 |

FOREIGN PATENT DOCUMENTS 9221981  12/1992  WIPO.

OTHER PUBLICATIONS

Kataoka et al. (II), "Studies on the Synthesis of Compounds Related to Adenosine 3', 5'–Cyclic Phosphate. VII. Synthesis and Cardiac Effects of $N^6$, $N^6$–Dialkyl Adenosine 3' 5'–Cyclic Phosphates," *Chem. Pharm. Bull.*, 38(11), 3147–3154 (Nov. 1990).

Allen et al., "Enhancement of Interfereon Antiviral Action in L–Cells by Cyclic Nucleotides," *Proc. Soc. Exp. Biol. Med.*, 146(2), 580–584 (1974)$^†$; *Chem. Abstr.*, 82(9), p. 75, Abstr. No. 51914b (Mar. 3, 1975); only abstract supplied.

Hayashi et al., "Regulation of Steroidogenesis by Adrenocorticotropic Hormone in Isolated Adrenal Cells," *J. Biol. Chem.*, 254(14), 6678–6683 (Jul. 25, 1979).

Cheitlin et al., "The Role of Extracellular Calcium in Corticotropin–Stimulated Steroidogenesis," *J. Biol. Chem.*, 260(9), 5323–5327 (May 10, 1985).

Carsia et al.(I), "Ontogenic Corticosteroidogenesis of the Domestic Fowl: Response of Isolated Adrenocortical Cells," *Proc. Soc. Expl. Biol. Med.*, 184(4), 436–445 (Apr. 1987).

Carsia et al.(II), "Effect of 3, 3'-Iminodiproprionitrile (IDPN) on Corticosteroidogenesis of Isolated Adrenocortical Cells," *Proc. Soc. Expl. Biol. Med.*, 184(4), 461–467 (Apr. 1987).

Ray et al., "Activation of the Human $\beta_2$–Interferon/Hepatocyte–Stimulating Factor/Interleukin 6" Promoter by Cytokines, Viruses, and Second Messenger Agonists," *Proc. Nat. Acad. Sci. USA*, 85, 6701–6705 (Sep. 1988).

Misaki et al., "Effects of Rat $\gamma$– and Non–$\gamma$–Interferons on the Expression of Ia Antigen, Growth, and Differentiated Functions of FRTL5 Cells," *Endocrinology*, 123(6), 2849–2857 (Dec. 1988).

Kone et al., "Role of NF–$\kappa$B in the Regulation of Inducible Nitric Oxide Synthase in an MTAL Cell Line," *Am. J. Physiology; Renal, Fluid and Electrolyte Physiology*, 38(5), F718–F729 (Nov. 1995).

Matsumori et al., "Inotropic Agents Differentially Inhibit the Induction of Nitric Oxide Synthase by Endotoxin in Cultured Macrophages," *Life Sciences Including Pharmacology Letters*, 59(10), PL121–PL125 (Aug. 2, 1996).

Ragsdale et al., "Loss of Fc Receptor Activity After Culture of Human Monocytes on Surface–Bound Immune Complexes," *J. Exp. Medicine*, 151(1), 32–44 (Jan. 1980).

Tutton et al., "Effects of Cyclic–Nucleotide Derivatives on the Growth of Human Colonic Carcinoma Xenografts and on Cell Production in the Rate Colonic Crypt Epithelium," *British J. Cancer*, 44(2), 182–188 (Aug. 1981).

Calkins et al., "Interleukin–1 Inhibits Leydig Cell Steriodogenesis in Primary Culture," *Endocrinology*, 123(3), 1605–1610 (Sep. 1988).

Ramage et al., "Growth Inhibition by 8–Chloro Cyclic AMP of Human HT29 Colorectal and ZR–75–1 Breast Carcinoma Zenografts is Associated with Selective Modulation of Protein Kinase A Isozymes," *European J. Cancer*, 31A(6), 969–973 (1995).

Nichols et al., "Induction of Ornithine Decarboxylase in Macrophages by Bacterial Liposaccharides (LPS) and Mycobacterial Cell Wall Material," *Life Sciences*, 27(11), 913–920 (Sep. 15, 1980).

Golos et al., "Regulation of Low Density Lipoprotein Receptor Synthesis in Cultured Luetinized Human Granulosa Cells by Human Chorionic Gonadotropin and 8–Bromo–cyclic AMP," *J. Biol. Chem.*, 260(27), 14399–14402 (Nov. 25, 1985).

Knepel et al., "Effect of Prostaglandin $E_2$ on ACTH and $\beta$–Endorphin Release from Rat Adenohypophysis in vitro After Secretagogues Which Can Mimic Various FIrst or Second Messengers," *Naunyn–Schmiedeberg's Arch. Pharmacology*, 333(2), 149–155 (Jun. 1986).

Yamashita et al., "Regulation of Human Growth Hormone Gene Expression by Insulin–like Growth Factor I in Transfected Cells," *J. Biol. Chem.*, 262(27), 13254–13257 (Sep. 25, 1987).

(List continued on next page.)

*Primary Examiner*—Marian C. Knode
*Assistant Examiner*—L. Eric Crane
*Attorney, Agent, or Firm*—Harris F. Brotman

[57] ABSTRACT

Methods for inducing immunosuppression in animals which need immunosuppressive treatment involving administration to animals of a therapeutically effective amount of the cyclic AMP agent HE-33 or its nucleoside.

4 Claims, 3 Drawing Sheets

OTHER PUBLICATIONS

Maus et al., "Treatment of Intact Striatal Neurones with Cholera Toxin of 8–Bromoadenosine 3', 5'–(Cyclic) Phosphate Decreases the Ability of Pertussis Toxin to ADP–Ribosylate the α–Subunits of Inhibitory and Other Guanine–Nucleotide–Binding Regulatory Proteins, $G_i$ and $G_o$ — Evidence for Two Distinct Mechanisms," *European J. Biochemistry*, 196(2), 313–320 (Mar. 1, 1991).

Pinto et al., "Inhibition of the Self–Renewal Capacity of Blast Progenitors from Acute Myeloblastic Leukemia Patients by Site–Selective 8–Chloroadenosine 3', 5'–Cyclic Monophosphate," *Proc. Nat. Acad. Sci. USA*, 89, 8884–8888 (Oct. 1992).

Wallach et al., "Hormonal Protection of Interferon–Treated Cells Against Double–Stranded RNA–Induced Cytolysis," *FEBS Letters*, 101(2), 364–368 (May 1979).

Bruynzeel et al., "Pentoxifylline Inhibits T–Cell Adherence to Keratinocytes," *J. Invest. Dermatology*, 104(6), 1004–1007 (Jun. 1995).

Durante et al., "Cyclic Nucleotide Regulation of Interleukin–1β Induced Nitric Oxide Synthase Expression in Vascular Smooth Muscle Cells," *Thrombosis Research*, 75(1), 63–71 (1994).

Vallée et al., "Regulation of Guinea Pig Adrenal P450c21 Messenger RNA, Protein and Activity by RU486," *J. Steroid Biochem. Mol. Biol.*, 54(1/2), 31–38 (Jul. 1995).

Novogrodsky et al., "Selective Suppression by Adherent Cells, Prostaglandin, and Cyclic AMP Analogues of Blastogenesis Induced by Different Mitogens," *J. Immunology*, 122(1), 1–7 (Jan. 1979).

Berkow et al., *The Merck Manual of Diagnosis and Therapy*, Merck and Co., Rahway, NJ, 1992, only pp. 338–342, 1305–1313, 1317–1320, 1337–1341 and 2435–2436 supplied.

Roth et al., "Complexing of Riboflavin and Its 2'–Substituted Analogs with Adenosine and Other 6–Substituted Purine Derivatives," *Photochemistry and Photobiology*, 6, 657–664 (1967).

METHODS FOR IMMUNOSUPPRESSING

This application is a continuation-in-part application of U.S. patent application Ser. No. 08/688,002, filed Jul. 29, 1996, now U.S. Pat. No. 5,747,474.

BACKGROUND OF THE INVENTION

1. Field of the Invention

This invention relates to immunosuppressive agents and their use in transplantation therapy. In particular, the invention is directed to the use of cyclic AMP compounds, their nucleoside derivatives, and agonists thereof for suppressing graft rejection.

2. Background Art

Many human diseases are characterized by excessive or inappropriate immune responses. In transplantation, the immune system attacks major histocompatibility complex (MHC)-disparate donor tissue leading to graft rejection. In autoimmune disease, the immune system attacks normal tissues. In allergy, the immune system is hyperresponsive to otherwise harmless environmental antigens. It is now recognized that immunosuppressive therapy is appropriate for treating each of these disorders (Blood Reviews, 1995, 9:117–133).

There has been a phenomenal increase in the success of organ transplants since the 1950s, and transplantation has become the treatment of choice for end-stage renal and cardiac failure. A number of advances have recently been made in understanding immune regulation, and in the development and use of immunosuppressive therapies (Thomson, A. W. et al., Immunol.. Rev., 1993, 136:71–98; Allison, A. C. et al. eds, 1993, Ann. NY Acad. Sci. 696:1–419; Kahan, B. D., 1994, Therapeutic Immunol.. 1:33–44; Thomson, A. W., et al., eds., 1994, Immunosuppressive Drugs, London: Edward Arnold). Although the development of drugs such as cyclosporin A (CsA) and FK506 has led to substantial improvements in preventing graft rejection, especially over the first year (Sigal, N. H., et al, 1992, Ann. Rev. Immunol.. 10:519–560; Thomson, A. W., et al., 1994, Clin. Exp. Immunol.. 98:351–357), there are serious side effects associated with use, such as nephrotoxicity and neurotoxicity (Kahan, B. D., et al., 1985, Surgery 97:125). In addition, the widely used immunosuppressive drugs are not soluble or orally available in pill form, and require administration by injection.

Graft-versus-host disease (GVHD) occurs when genetically disparate lymphocytes are transferred into an immunologically compromised recipient incapable of rejecting the donor graft (Billingham, R. E. Harvey, Lect,, 1967, 62: 21–78; Nash, R. A. and Storb, R., Current Opinion in Immunology, 1996, 8: 674–680). Acute GVHD is a major and frequent complication of bone marrow transplantation (BMT) (Ferrara, J. L. M. et. al., Transplantation, 1989, 47: 50–54). Although T cells are clearly required for the induction of the disease in both clinical and animal models of BMT, natural killer (NK) cells have been implicated in target tissue damage (Ferrara, J. L. M. et. al., Transplantation, 1989, 47: 50–54; Ghayur, T. et. al., Transplantation, 1987, 44: 261–267; Nash, R. A. and Storb, R., Current Opinion in Immunology, 1996, 8: 674–680). Prevention of GVHD has been attempted most often with pharmacological immunosuppression. The most commonly used agents are cyclosporine-A (CsA), methrotrexate, prednisone and FK506 (Storb, R. et. al., New England Journal of Medicine, 1986, 314: 729–735; Storb, R. et. al., Blood, 1990, 76: 1037–1045; Nash, R. A. et. al., Blood, 1995, 85: 3746–3753). However, these agents have potential side effects, such as nephrotoxicity, increased hair growth on the body, and neurotoxicity (Kahan, B. D. et. al., Surgery, 1985, 97: 125; Fay, J. W. et. al., Blood, 1996, 87: 3514–3519). There is, therefore, a clinical need to provide new compounds for effective immunosuppression without these side effects and with greater ease of administration.

DISCLOSURE OF THE INVENTION

The present invention is directed to methods for inducing immunosuppression in recipient animals which need immunosuppressive treatment, and directed to methods for inducing immunosuppression of a donor prior to transfer of donor tissue to recipient to prevent graft failure in the recipient.

The method comprises administering to a recipient or to a donor animal a therapeutically effective amount of the cyclic AMP agent HE-33, or the corresponding nucleoside derivative of HE-33, or agonists thereof. An embodiment of the invention involves administering HE-33 or its nucleoside in association with a physiologically acceptable pharmaceutical carrier or diluent. A further embodiment involves administering HE-33 or its nucleoside in combination or association with one or more agents selected from a group of immunosuppressing agents or agents useful in immunosuppressive therapy. The invention also features a pharmaceutical composition comprising a therapeutically effective amount of HE-33 or its nucleoside in association with one or more agents selected from the group of immunosuppressive agents or agents useful in immunosuppressive therapy.

MODES OF CARRYING OUT THE INVENTION

General Description and Definitions

The practice of the present invention will employ, unless otherwise indicated, conventional molecular immunology, cell biology, biochemistry, and organic synthesis within the skill of the art. Such techniques are explained fully in the literature. See, e.g. Abbas, A. K., et al., eds, 1994, 2nd ed. Cellular and Molecular Immunology, W. B. Saunders Co., USA; Harlow, E. and D. Lane, Antibodies, A Laboratory Manual, Cold Spring Harbor Laboratory, 1988; Auchinclos, Jr., H. and Sachs, D. H. Transplantation and Graft Rejection in: Fundamental Immunology, Paul, W. E. ed., 1993, Raven Press).

The following terminology will be used in accordance with the definitions set out below in describing the present invention.

For purposes of the invention, the term "immunosuppressive treatment" refers to an approach to the prevention and management of diseases and syndromes, which require for therapy the suppression of lymphocytes and immunocytes. Such diseases and syndromes include, but are not limited to, graft vs. host disease, autoimmune diseases such as diabetes, rheumatoid arthritis, systemic lupus erythematosus, Sjogren's Syndrome, and scleroderma. It is understood that a commonly used method of immunosuppression involves administering to an animal in need of such treatment an effective amount of an immunosuppressive agent in order to inhibit or lyse T cells.

The term "lymphocytes and immunocytes" refer to cells that mediate the specificity of immune responses. As used herein, the terms refer to T lymphocytes, which are described in detail in Abbas et al.

The term "transplantation" refers to the process of taking cells, tissues, or organs, called a graft, from one individual and, usually, placing them into a different, genetically non-identical recipient. The individual who provides the graft is referred to as the donor, and the individual who receives the graft is referred to as either the recipient or host. Transplantation leads to a specific immune response, called rejection, that can destroy the graft. Transplant tissues include solid organs, such as liver, heart, and kidneys; tissues such as skin and bone marrow, or other cells or tissues. In vivo rejection is mediated by T cells. It is well known in the art that rejection may be prevented or treated by recipient (host) immunosuppression. Most immunosuppression is directed at T-cell responses using specific immunosuppressive agents. Transplant recipients require preparatory immunosuppression prior to receiving a transplant. For example, rejection may be prevented or treated by immunosuppressing the recipient (host) by administering to the host therapeutically effective amounts of compounds such as cyclosporin A or FK506, as well as administering the compositions exemplifed herein. Most immunosuppression is directed at T-cell responses using specific immunosuppressive agents, not unlike the compositions of the present invention.

When mature T lymphocytes are injected into a non-identical immunoincompetent recipient, they can recognize the recipient host as foreign and attack the recipient causing a graft-versus-host (GVH) reaction and failure of the graft. In human patients, mature T cells in allogenic bone marrow grafts cause graft-versus-host disease.

Accordingly, immunosuppression of NK cell function in donors plays an important therapeutic role in treating or preventing graft-versus-host reactions such as graft versus host disease (GVHD). "Natural killer cells" or "NK cells" are non-T, non-B lymphocytes usually having granular morphology. NK cells are important in innate immunity to viruses and other intracellular pathogens as well as in antibody-dependent cell-mediated cytotoxicity (ADCC). NK cells are responsible in large degree for graft versus host disease (GVHD) (Ferrara, J. L. M., et al. (1989) Transplantation 47:50–54; Ghayur, T. et al. (1987) Transplantation 44:261–267; Ghayur, T., et al. (1988) Transplantation 45:586–590. As demonstrated in the Examples below, it was found that the compounds and methods of the invention suppressed NK cell activity in vivo and found use in preventing or overcoming GVHD in animals in need of such treatment. Accordingly, transplant donors require preparatory immunosuppression by administration of a therapeutically effective amount of an immunosuppressive agent prior to donating a transplant for prevention of graft versus host disease in a recipient.

The term "animals" is taken to mean humans as well as other animals.

The term "HE-33 and its nucleoside" refers to the nucleotide agent HE-33, which is a cyclic adenosine monophosphate (AMP), as described below, and HE-33's corresponding nucleoside, referred to below as compound 1–46. The chemical structures of "HE-33 and its nucleoside" are illustrated in Formulas I and II, respectively.

The term "HE-33 and its nucleoside" is also understood to include agonists of HE-33 and its nucleoside. Accordingly, HE-33 includes agonists of HE-33 wherein

$R_1$, $R_2$ are same or different or in any independent combination of $R_1$=H, —$(CH_2)_n$ OH where n=1–5; alkyl C1 to C12 substituted or unsubstituted, straight chain or branched, 0–6 double bonds $R_3$, $R_4$, $R_5$ are same or different or in any independent combination of $R_3$=H, Cl, Br, F, I, $NH_2$, $NHR_1$, $N(R_1)_2$, OH, OR, SH, $SR_1$ $R_6$=H, $NH_4^+$, $Na^+$ and other physiologically acceptable cations $R_6$=N-alkyl (mono, di and tri substituted) linear and branched chain $C_1$ to $C_6$ It is understood that the term "agonists of HE-33" as used herein refers to substances that elicit the same response (i.e. inducing imimunosuppression in animals in need of such treatment) as HE-33. Agonists of HE-33 include the above-enumerated derivatives or structural modifications of HE-33. An examples of an agonist of HE-33 is compound 1–24 (see Table 1).

It will be understood that 1–46 includes agonists of 1–46 wherein $R_1$, $R_2$ are same or different or in any independent combination of $R_1$=H, —$(CH_2)_n$OH where n=1–5; alkyl C1 to C12 substituted or unsubstituted, straight chain or branched, 0–6 double bonds $R_3$, $R_4$, $R_5$ are same or different or in any independent combination of $R_3$=H, Cl, Br, F, I, $NH_2$, $NHR_1$, $N(R_1)_2$, OH, $OR_1$, SH, $SR_1$ It is understood that the term "agonists of 1–46" as used herein refers to substances that elicit the same response (i.e. inducing immunosuppression in animals in need of such treatment) as 1–46. Agonists of 1–46 include the above-enumerated derivatives or structural modifications of 1–46.

All of the just-mentioned agonists of HE-33 or its nucleoside are contained in articles and publications recited below (in the sections entitled "Compounds of the Invention" and "Compound Preparation") which can be used to practice the present invention and are hereby incorporated by reference. The ability of an analog or deriviative of HE-33 or its nucleoside to induce immunosuppression in animals in need of such treatment in the method of the invention is readily determined by screening the analog or deriviative with the screening methods enumerated herein for identifying agonists.

The methods of the present invention are directed to immunosuppressive therapy using the agent HE-33 (1–18) or its nucleoside (1–46), and agonists thereof. Both HE-33 and 1–46 are useful because they exhibit pharmacological activity in animals, as set forth below (see Tables 3 and 9). In particular, the methods of the present invention involve administering to an animal in need of such treatment a therapeutically effective amount of agent HE-33 or its nucleoside. A further embodiment of the invention comprises administering to a transplantation donor a pharmaceutical composition comprising a therapeutically effective amount of HE-33 or its nucleosidethe compound in order to prevent or ameliorate GVHD in the recipient. All embodiments of the invention involve associating HE-33 or its nucleoside with a pharmaceutical carrier or diluent for administration to an animal.

The method of the invention finds use in suppressing the rejection of transplants in animals, as illustrated by the effects of HE-33 and its nucleoside on cellular immunity in the one-way and two-way MLR tests set forth below (See Tables 1 and 2). Thus, the method of the invention is useful in the suppression of the formation of, or proliferation of immunocytes or lymphocytes, and is therefore useful in the treatment of autoimmune diseases, and in suppressing the rejection of transplants, e.g. organ transplants, such as skin, bone marrow, kidney, liver and heart transplants. The effects of HE-33 and its nucleoside were ascertained in the tests described below.

Figure 1:
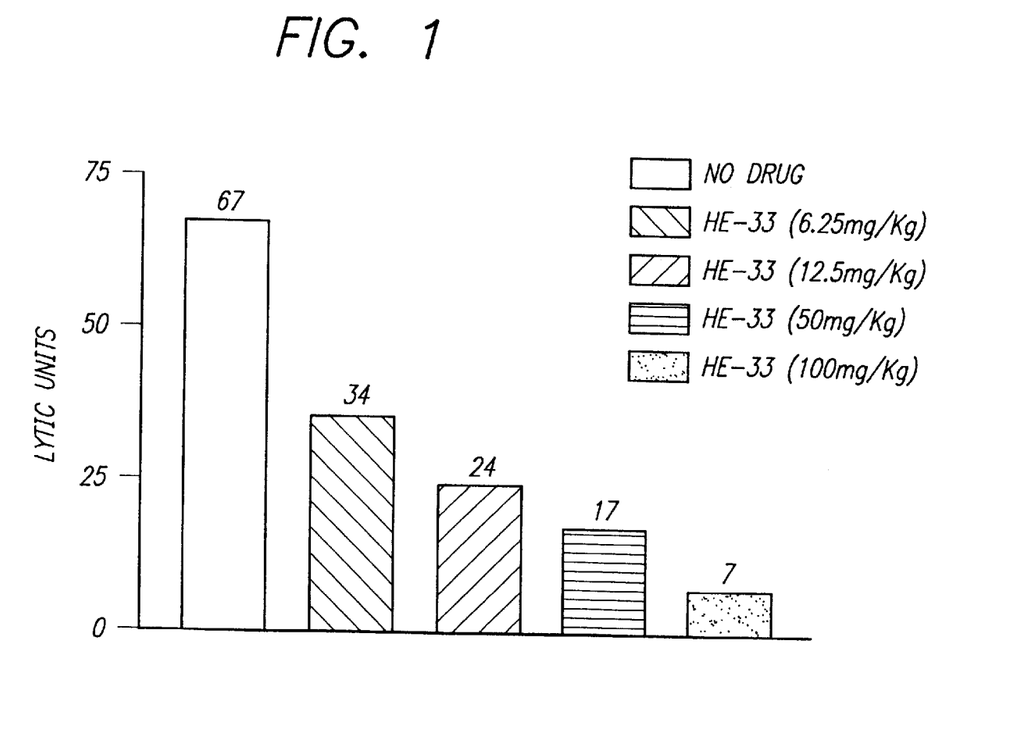
FIG. 1 shows the inhibitory effect of HE-33 in vivo on the generation of $H-2^k$ anti-$H-2^d$ cytotoxic T-cell activity.

As indicated by FIG. 1, and in Tables 3, 4 and 5, the method of the invention finds use in treating autoimmune diseases in animals. It is understood that immunosuppressants for T-cells, such as cyclosporin A (Forsell, T et al., J. Urol, 1996, 5:1591–3; Yocum, D. E., et al., Rheum. Dis. Clin. North. Am., 1995, 3: 835–44) or tacrolimus (Ketel, B. L., et al., Transplant. Proc., 1996, 2:899) suppresses immune reactions and result in inhibition or amelioration of autoimmune disorders. T-cells and their products (cytokines) are known to be involved in the generation and production of autoimmune reactions in vivo.

For all of the above-mentioned uses, the therapeutic effective amount or dosage will, of course, vary depending on the compound employed, mode of administration and treatment desired. However, in general, satisfactory results would be obtained when administered orally at a daily dosage of from about 1 mg to about 600 mg per kg animal body weight, conveniently given in divided doses 1 to 4 times a day or in sustained release form. If administered by injection, in general, satisfactory results would be obtained when administered orally at a daily dosage of from about 1 mg to about 200 mg per kg animal body weight, conveniently given in divided doses 1 to 4 times a day or in sustained release form. For the larger mammals, the total daily dosage would be in the range of from about 5 to about 500 mg, and dosage forms suitable for oral administration comprise from about 5 mg to about 500 mg of the compounds admixed or in association with a solid or liquid pharmaceutical carrier or diluent. Methods are well known in the art for determining therapeutically effective amount of HE-33 or its nucleoside. Such methods involve analysis of the pharmaceutical/pharmacokinetic parameters in immunosuppressive therapy for inducing immunosuppression, for suppressing formation of lymphocytes and immunocytes, for treating autoimmune diseases, and for suppressing rejection of transplants in animals or other indications (Recent Developments in Transplantation Medicine, Vol. 1: New Immunosuppressive Drugs: eds. D. Przepiorka and H. Sollinger, Physicians and Scientists Pub. Co., Glenview, Ill., 1994;).

The method of the present invention includes administering a pharmaceutical composition comprising an effective amount of HE-33 or its nucleoside in pure form or as a pharmaceutically acceptable crude concentrate in association with a pharmaceutical carrier or diluent. Such compositions conveniently contain more than 1% by weight of the compound of formula I or II and may be prepared by conventional techniques to be in conventional forms, for example, capsules, tablets, suppositories, dispersible powders, syrups, elixirs, suspensions or solutions for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period. Other compounds and methods known in the art for delaying disintegration or for timed-delayed or time-measured delivery of the active ingredients also find use in formulating the active ingredients for use in the methods of the invention. For example, HE-33 or its nucleoside may also be combined with liposomes or other delayed-release carrier means to protect HE-33 or its nucleoside thereof from degradation until they reach their targets and/or facilitate movement of HE-33 or its nucleoside across tissue barriers.

The preferred compositions from the standpoint of ease of administration are solid compositions, particularly solid-filled gelatin capsules or tablets.

It is also to be understood that a further embodiment of the method of the invention involves combining one or more agents in a variety of protocols, including prophylaxis, with the method of the invention for administering to animals in need of immunosuppressive treatment HE-33 or its nucleoside. Combination protocols and methods for determining their efficacy, including therapeutic drug monitoring, are well known in the art (Lazarus, H. M. et al. Blood Reviews, 1995, 9:117–133; Aggarwal, B. B., et al., eds., 1995, Human Cytokines: Their role in Disease and Therapy, Blackwell Science, Inc., Cambridge, Mass.; Ambrus, J. L. et al., 1993, Surgery, Gynecology & Obstetrics, 176:588). Examples of immunosuppressive agents or agents useful in immunosuppressive therapy which may be combined with administering HE-33 or its nucleoside in the method of the invention include, but are not limited to corticosteroids, methotrexate, cyclosporin, rapamycin, FK506 (Prograf™), antithymocyte globulin, monoclonal antibody preparations, polyclonal antibody preparations, interleukin 1 antagonists, interleukin 2 antagonists, TNF antagonists, immunotoxins, thalidomide, interferon, nitric oxide, mizoribine, deoxyspergualin, leflunomide, and anti-adhesion molecules.

It will be further understood that the present invention includes a pharmaceutical composition comprising a therapeutically effective amount of HE-33 or its nucleoside in association with one or more agents selected from the group of immunosuppressive agents or agents useful in immunosuppressive therapy consisting of corticosteroids, methotrexate, cyclosporin, rapamycin, FK506 (Prograf™), antithymocyte globulin, monoclonal antibody preparations, polyclonal antibody preparations, interleukin 1 antagonists, interleukin 2 antagonists, TNF antagonists, immunotoxins, thalidomide, interferon, nitric oxide, mizoribine, deoxyspergualin, leflunomide, and anti-adhesion molecules. Methods are well known in the art for determining therapeutically effective amounts of HE-33, its nucleoside, and agents selected from the group of immunosupprssive agents or agents useful in immuosuppressive therapy in association with HE-33 when associated in the composition of the invention ((Lazarus, H. M. et al. Blood Reviews, 1995, 9:117–133; Aggarwal, B. B., et al., eds., 1995, Human Cytokines: Their role in Disease and Therapy, Blackwell Science, Inc., Cambridge, Mass.; Ambrus, J. L. et al., 1993, Surgery, Gynecology & Obstetrics, 176:588).

The following materials and methods were employed in the non-limiting Examples set out below.

Blood donors. Heparinized blood (30 cc) was obtained by venipuncture from volunteers. Two donors of different genetic backgrounds are usually required to initiate a mixed leukocyte culture (MLC).

Culture medium. RPMI-1640 medium (Fisher Scientific Co., Santa Clara, Calif.) was supplemented with 20% heat-inactivated human AB serum and 1% penicillin/streptomycin mixture.

Isolation of mononuclear leukocytes. Mononuclear leukocytes were isolated from the blood by layering appropriately diluted blood in Hanks-balanced salt solution (H-BSS) on ficoll-hypaque gradient followed by centrifugation. The recovered cells were washed three times in culture medium, and viability was determined by trypan blue dye exclusion method. Cell concentration was adjusted to $2\times10^6$/ml in complete culture medium.

Mixed leukocyte reaction (MLR)

The MLR is an in vitro model of T-cell recognition of foreign major histocompatibility complex (MHC) gene products and was used as a predictive test of cell-mediated graft rejection (Abbas, A. K., et al., eds, 1994, 2nd ed. Cellular and Molecular Immunology, W. B. Saunders Co., USA). It is well known in the art that the MLR is induced by co-culturing mononuclear leukocytes from one individual with mononuclear leukocytes derived from another individual. If there are differences in the alleles of the MHC genes between the two individuals, a large proportion of the mononuclear cells will proliferate over a period of 4–7 days. The level of proliferative response is measured by incorporation of $^3$H-thymidine into DNA during cell replication and is referred to as allogeneic MLR. Because the cells from each donor react and proliferate against the other, the resultant response is known as a "two-way MLR." HE-33, its nucleoside, and other candidate compounds were tested in the MLR for their ability to "immuosuppress."

"Two-way MLR" set up in microtiter plates

Mononuclear cells (at $2\times10^6$/ml) of each donor were first mixed thoroughly together in a 50 ml tube at a 1:1 ratio with volume. The mixture was dispensed into wells of a 96-well U-bottom microtiter plate in volumes of 100 µl per well. Compounds or suspected immunosuppressive agents were added in culture medium in volumes of 100 µl per well at varying concentrations of 100, 10, 1, 0.1 or 0.01 µM, respectively. 100 µl of culture medium was added to control wells without drug. Cultures were maintained in a humid incubator at 37° C. in an atmosphere of 5% $CO_2$ for 5 days. At 4 hours before harvest, the cultures in each well were pulsed with 1 µCi of tritiated thymidine (specific activity 719.5 mCi/mg; Dupont, Wilmington, Del.). Cells were harvested onto glass fiber filters (Packard, Downers Grove, Ill.) with a 96-well automatic cell harvester (TOMTEC, Hamden, Conn.) and were counted directly on a Matrix 9600 beta counter (Packard). The results are shown in Table 1 and in FIG. 2.

Data was expressed as percent inhibition (% Inhibition) according to the following formula:

$$\% \text{ Inhibition} = 100 - \left(\frac{\text{Counts per minute (CPM) for wells with drug}}{\text{CPM for wells without drug}} \times 100\right)$$

Generation of MHC-restricted Cytolytic CD8+ T-lymphocytes in "One-way Human MLR" Cultures The "one-way MLR" was set up in tissue culture flasks with mononuclear cells from two different donors as in the "two-way MLR" described above. However, in "one-way MLR," one of the two mononuclear leukocyte populations was rendered incapable of proliferation by treatment with mitomycin C, an antimitotic drug, prior to culture. In this "one-way MLR," the treated cells served exclusively as stimulators and the untreated cells, still capable of proliferation, served as the responders. The responder cells, during a 5–7 day culture period, expressed the CD8+ phenotype but not the CD4+. These CD8+ cells served exclusively as cytolytic T lymphocytes (CTLs) which lyse target cells from the same individual as the original stimulator cell population. In transplantation, these MHC-restricted cytotoxic CD8+ T-cells lyse MHC disparate donor tissue targets, leading to graft rejection (Abbas, A. K., eds., 1994, 2nd ed., Cellular and Molecular Immunology, W. B. Saunders Co., USA; Imagawa, D. K., et al., in Aggarwal, B. B., et al., eds., 1995, Human Cytokines: Their role in Disease and Therapy, Blackwell Science, Inc., Cambridge, Mass.). The results are shown in Table 2.

"One-way MLR" Set up in Tissue Culture Flasks

Mononuclear cells of one donor were first treated with mitomycin C (Sigma Chem. Co., St. Louis, Mo.) (50 µg/50× $10^6$ cells) in 15 mL tubes wrapped in aluminum foil and incubated in a 37° C. water bath for 1 hr. At the end of incubation, cells were washed 3 times with tissue culture medium and adjusted to $2\times10^6$/mL and mixed at a 1:1 ratio with volume and incubated in tissue culture flasks for 5–7 days in the presence of either 100 µM HE-33, CsA or medium only. Some of the stimulator cells which were not mitomycin C-treated were cultured in IL-2-conditioned media for use as targets at the end of 5 or 7 days.

CTL Assay

At the end of the culture period, target cells were labeled with $^{51}Na_2CrO_4$ ($^{51}$Cr) and adjusted to $0.5\times10^6$/mL. Effector cells (i.e., responder cells) were harvested, washed twice in medium and live cells were adjusted to $2.5 \times 10^6$/mL. Effector and target cells were mixed at an effector:target (E:T) cell ratio of 25:1 in 96-well U-bottom microtiter plates and incubated for 4 hr. in a 37° C./5% $CO_2$ incubator. At the end of incubation, lysis of target cells was assessed essentially as described previously for a $^{51}$Cr-release assay (Ojo-Amaize, E. A., et al., 1994, Clin. Infect. Dis. 18 (Suppl.) :S154–159) and results expressed as % specific lysis.

Generation of H-2 Restricted Cytolytic T-lymphocytes in Mice

A mouse correlate of the human "one-way MLR" was developed in inbred strains of mice. The cells of one mouse strain (H-$2^d$) were injected i.v. into a different mouse strain (H-$2^k$). Mice were obtained from Charles River Laboratories, Hollister, Calif.). Because of the histoincompatibility between the two strains, the H-$2^k$ mice develop cytotoxic T-cells capable of killing the cells of the H-$2^d$ strain of mice (Abbas, A. K., id), which is the type of reaction observed in humans or animals receiving tissue grafts from histoincompatible donors. The H-$2^k$ mice sensitized against H-$2^d$ cells/allo-antigens were treated with either HE-33 (100 mg/kg i.v. or 400 mg/kg orally) every three days for 9 days or were not treated with drug. The results are shown in Table 3.

Ex Vivo Assay. On the tenth day, all mice were sacrificed, and spleens were removed to test for splenic T-cell-mediated cytotoxicity against CON-A stimulated DBA/2 spleen cells expressing the H-$2^d$ antigens. CON-A was obtained from Sigma Chem. Co., St. Louis, Mo. Spleen cell suspensions were prepared in complete culture medium and adjusted to desired concentrations. The CON-A blast cells were radiolabeled with $^{51}$Cr and mixed with the respective splenic effector cells at varying effector:target cell ratios in 96-well microtiter plates. The mixtures were cultured for 4 hr. at 37° C. in a 5% $CO_2$ incubator. Lysis of target cells were assessed essentially as described previously for a $^{51}$Cr-release assay (Ojo-Amaize, E. A., et al., id) and results expressed as % specific lysis (FIG. 1).

Production of autocrine growth factors (IL-2, IL-4, IL-10 and Interferon-gamma) in PHA-stimulated human PBMC cultures Human peripheral blood mononuclear cells (PBMC) were cultured with T-cell mitogen, PHA (Gibco BRL, Grand Island, N.Y.) (3 µg/mL) at $2 \times 10^6$/mL in 1.0 rmL volumes in 24-well plates in the presence of either 10 µM HE-33, CsA, 10 ng FK506 or medium for varying periods of time (24, 48, 72 or 96 hr., respectively) in a 37° C. incubator with 5% $CO_2$. Culture supernatants were collected at the times indicated and frozen at −20° C. At the end of 96 hr., all supernatants were assayed by enzyme immunoassay for the presence of the cytokines: interleukin-2, -4, -10 and interferon (IFN)-gamma. Results were expressed in pg/mL concentration of cytokine and % inhibition of cytokine production. The results are shown in Table 4.

Induction of antigen-specific T cell proliferation

PBMC of a laboratory volunteer who had received three months prior a booster shot of tetanus toxoid (TTX) vaccine was tested for a secondary proliferative response to TTX antigen in vitro in the presence or absence of HE-33 (1 or 10 µM) and CsA (10 or 100 µM). Proliferative response was determined by incorporation of $^3$H-thymidine into DNA of dividing cells. The results, shown in Table 5, were expressed in counts per minute (CPM) and % inhibition of proliferation.

Anti-T cell receptor (TCR)/CD3 induced T cell proliferation

PBMC of a healthy volunteer were cultured in 96-well microtiter plates at $2 \times 10^5$ cells/well. The cells were stimulated with anti-CD3 monoclonal antibody (Pharmingen, San Diego, Calif.) at 1 ng/mL concentration in the presence of either HE-33 (10 µM, 100 µM), CsA (100 µM) or medium. Cultures were incubated for 3 days at 37° C. in a 5% $CO_2$ incubator. Proliferative response was determined by incorporation of $^3$H-thymidine. As shown in Table 6, the results were expressed in CPM and % inhibition of proliferation.

Determination of the effect of HE-33 on PK-C-mediated signaling pathway

PBMC of a healthy volunteer were cultured in 96-well microtiter plates at $2 \times 10^5$ cells/well. The cells were stimulated with optimal stimulating doses of phorbol myristate acetate (PMA) (1.25 ng/mL) and calcium ionophore (A23187))(Sigma Chem. Co., St. Louis, Mo.) (0.25 µM) in the presence of 100 µM concentrations of HE-33, I-24, dbcAMP, CsA, Forskolin (Sigma Chem. Co.), or medium. Forskolin is an agent well known to increase intacellular cAMP levels by activating adenylate cyclase. Cultures were incubated for 3 days at 37° C. in a 5% $CO_2$ incubator. Proliferative response was determined by incorporation of $^3$H-thymidine.. The results were expressed in CPM and % inhibition of proliferation (Table 7).

Single dose range-finding study of HE-33 in mice

Swiss Webster mice (Charles River Laboratories, Hollister, Calif.) were used for the preliminary toxicology study. One mouse per dose level was administered a single intravenous (IV) dose of either 1.5, 15, 75, 100, 150, 200, 300 or 400 mg of HE-33/kg body weight. The dose volume for all mice receiving saline or formulations of HE-3 3 was 10 mL/kg body weight. All doses were administered as a slow-push IV injection in the tail vein. Day 1 of the study for each mouse occurred on the day of administration of the drug or the saline.

Clinical observations/body weights

Each mouse was observed closely for clinical signs of toxicity at approximately 10, 30 and 60 minutes and 5 hours after dosing on Day 1, and once daily on Days 2–8. In addition, mortality checks were performed twice daily. Body weights were obtained on each mouse prior to dosing on Day 1. Body weights (Day 1) for the mice used in this study ranged between 27.3 and 32.5 g (Table 8).

Generation of $F_1$ Recipient Mice: Male mice of inbred strains, C57BL/6 (H-$2^b$ haplotype) were mated with female mice of inbred strains, $C_3$H/j (H-$2^k$ haplotype). The resulting hybrids (C57BL/6×$C_3$H/j)$F_1$ were used as recipients of the B6 spleen cells.

Elimination of endogenous and inducible NK cell activity from the cell donor mice (C57BL/6)

Six- to ten-week old C57BL/6 mice were treated for 24 hours orally or intravenously with HE-33. Orally-treated mice received 400 mg/kg twice a day (Bid), and intravenously treated mice received a single 100 mg/kg i.v.

NK Cell cytotoxicity assay: At the end of the 24 hour pre-treatment with HE-33, all treated mice and control, non-treated mice (i.e., mice treated with vehicle, PBS) were sacrificed by cervical dislocation. Spleens and lymph nodes were removed and single-cell suspension of pooled spleen and lymph nodes from mice in each group of donor were prepared in RPMI-1640 supplemented with 10% fetal bovine serum (FBS) and 1% penicillin/streptomycin. Target cells were $^{51}$Cr-labeled Moloney leukemia virus-induced lymphoma (YAC) tumor cells. Different effector:target cell ratios were cultured in triplicate samples in U-bottomed microtiter plates for 4 hours at 37° C. in a humidified atmosphere containing 5% $CO_2$. The microtiter plates were then centrifuged, and 100-$\mu$L aliquots of supernatants were assayed for $^{51}Cr$ release. Results were expressed as percent lysis and percent suppression of lysis. The method of Ojo-Amaize, E. et. al., *Scand. Journal of Immunology*, 1978, 7: 297–306, was used for the NK assays.

Irradiation of Recipient $(B_6 \times C_3H)F_1$ Mice: Ten- to twelve-week old $(B_6 \times C_3H)F_1$ mice were sublethally irradiated with a Cobalt-60 gamma source at 450 rads in a single dose.

Induction of GVHD: GVHD was induced in irradiated $(B_6 \times C_3H)F_1$ mice by the intravenous injection of $5 \times 10^7$ donor $B_6$ $(H-2^b)$ spleen and lymph node cells.

Assessment of GVHD: Mice were weighed weekly to document weight loss and were observed daily for hunched appearance, extensive dermatitis, diarrhea and, ultimately, death (Ferrara, J. L. M. et. al., *Transplantation*, 1989, 47: 50–54).

COMPOUNDS OF THE INVENTION

As depicted in Table 1, compounds synthesized and tested in the method of the invention include 3',5'-cyclic adenosine monophosphate derivatives (1–18, 1–5, 1–15, 1–16, 1–22, 1–24, 1–41, 1–42) or nucleosides (1–46, 1–49, 1–50). For reference, the techniques used in synthesizing the compounds modified at N-6 are based on the previously described method (Kataoka, S., et al., 1990), Chem. Pharm. Bull.38:3147–3154). For the 2'-O alkylations, the method of Tazawa, et al. (Biochemistry (1972)11:4931 –4937)) was used. (Abbas, A. K., et al., eds, 1994, 2nd ed. Cellular and Molecular Immunology, W. B. Saunders Co., USA

COMPOUND PREPARATION

2'-O-Tosyl-c-AMP (1–5)

To a solution of c-AMP (purchased from SIGMA Chemical Company) in dioxane was added an aqueous solution of sodium hydroxide. p-Toluenesulfonyl chloride was added and the mixture was stirred at room temperature overnight. The resulting white solid was filtered off, washed with cold dioxane and dried to yield title compound as an amorphous solid.

$N^6,N^6$-di-n-Propyl-2'-O-tosyl-c-AMP (1–15)

A solution of the above solid (1 –5) in dry N,N-dimethylformamide was treated with hexane washed sodium hydride and the resulting mixture was stirred at room temperature for 15 min. 3-Bromo-1-propane was added and the reaction mixture was stirred at room temperature overnight. The reaction was quenched by the addition of aqueous methanol, adsorbed onto silica gel and flash chromatographed with an increasing gradient (0 to 15%) of methanol in dichloromethane as eluent to yield pure product as amorphous off-white solid.

$N^6,N^6$-di-n-Propyl-c-AMP (1–18, i.e. HE-33)

The 2'-O-tosyl compound (1–15) was dissolved in methanol and treated with aqueous 2N sodium hydroxide. The resulting mixture was stirred at room temperature for two days. The mixture was adsorbed on silica gel and flash chromatographed with a mixture of ethyl acetate:methanol:acetone:water::7:1:1:1 as eluent. Appropriate fractions were pooled and concentrated in vacuo to yield the target compound or agent 1–18, i.e. HE-33 as a foam.

Agent HE-33 (1–18)

The chemical properties, synthesis, and isolation of agent 1–18, herein designated as HE-33, are described in Kataoka, S. et al. Chem. Pharm. Bull 38(11) 3147–3154 (1990); and in U.S. patent Ser. No. 5,246,922 in which several agonists of HE-33 are disclosed. U.S. patent Ser. No. 5,246,922 is hereby incorporated by reference.

Agent 1–46

The chemical properties, synthesis and isolation of agent 1–46 (see Formula II), referred to herein as the nucleoside of HE-33, are described in Roth, J. A. et al., Photochem. Photobiol. 6(9):657–64 (1967), and in which several agonists of 146 are disclosed.

Table 1 contains the following nucleotide compounds:

HE-33: R1=R2=n-propyl; R3=R4=H; R5=OH; R6=Na 1-15: R1=R2=n-propyl; R3=R4=H; R5=O-tosyl; R6=$NH_4$ 1-16: R1=n-propyl; R2=H; R3=R4=H; R5=OH; R6=$NH_4$ 1-22: R1=R2=n-butyl; R3=R4=H; R5=O-tosyl; R6=$NH_4$ 1-24: R1=R2=n-butyl; R3=R4=H; R5=OH; R6=$NH_4$ 1-42: R1=R2=n-propyl; R3=Benzyl-thiol; R4=H; R5=OH; R6=Na Table 1 contains the following nucleoside compounds:

1-46: R1=R2n -propyl; R3=R4=H; R5=OH 1-49: R1/R2=R1/R2=; R3=R4=H; R5=OH.

1-50: R1=R2=ethyl; R3=R4=H; R5=OH

RESULTS

As indicated by the following results, HE-33, its nucleoside and agonists thereof are useful as immunosuppressives, i.e., by their effect on cellular immunity, as indicated in standard tests described above. Accordingly, HB-33, its nucleoside are useful in the immunosuppression of the formation of, or proliferation of immunocytes or lymphocytes, and are therefore useful in supppressing the rejection of transplants, e.g. organ transplants such as skin, bone marrow and kidney transplants; and useful in treating autoimmune diseases. The effects of HE-33 and its nucleoside were determined in the tests described above, the results of which are set forth below.

Table 1 is representative of results from several experiments using different pairs of donors for each experiment. The results demonstrate that the inhibitory capacity of HE-33 on a 2-way MLR is comparable to that of cyclosporin (CsA). It can also be concluded that the inhibitory concentrations ($IC_{50}$), i.e., the drug concentration capable of inducing a 50% inhibition, is between 0.1 $\mu$M and 1 $\mu$M for both HE-33 and CsA, whereas the other modified forms of HE-33 (1–5,1–15,1–16,1–22 and 1–24 respectively) all had different $IC_{50}$s. Among these, however, compound 1–24 had significant inhibitory capacity, and finds use in the method and composition of the invention.

TABLE 1

2/31 Inhibitory Effect of HE-33, 1-46 and Derivatives on Two-way MLR

| Compound | % Inhibition | | | | |
|---|---|---|---|---|---|
| | 100 $\mu$M | 10 $\mu$M | 1 $\mu$M | 0.1 $\mu$M | 0.01 $\mu$M |
| HE-33(1-18) | 99.2 | 96 | 81 | 40 | 28 |
| CsA | 99.6 | 84 | 77 | 43 | 27 |
| Forskolin | 60 | 55 | 31 | 28 | 20 |
| 1-5 | 58 | 24 | 25 | 16 | 0 |
| 1-15 | 99.4 | 25 | 9 | 6 | 0 |

TABLE 1-continued

2/31 Inhibitory Effect of HE-33, 1-46 and Derivatives on Two-way MLR % Inhibition

| Compound | 100 μM | 10 μM | 1 μM | 0.1 μM | 0.01 μM |
|---|---|---|---|---|---|
| 1-16 | 99.8 | 90.7 | 12.5 | 2.2 | 0 |
| 1-22 | 99 | o | 4 | 7 | 0 |
| 1-24 | 1oo | 97 | 78 | 27 | 0 |
| 1-41 | 62 | 1 | 0 | — | — |
| 1-42 | 89 | 31 | 0 | — | — |
| 1-46 | 98 | 83 | 12 | — | — |
| 1-49 | 61 | 1o | 2 | — | — |
| 1-50 | 88 | 45 | 13 | — | — |

Table 2 shows the inhibitory effect of HE-33 on MHC class I-restricted cytotoxic T lymphocyte-mediated lysis of MHC-disparate stimulator target cells. In tissue rejection reactions, MHC-restricted cytotoxic CD8+ T-cells lyse MHC-disparate donor tissue, leading to graft rejection (Abbas et al., Cellular and Molecular Immunology, 1994, W. B. Saunders Co., USA; Imagawa, D. K., et al. in Aggarwal, B. B., et al., eds. Human Cytokines: Their Role in Disease and Therapy, Blackwell Science, Inc., Cambridge, Mass., 1995). In this experiment, it was demonstrated that HE-33 significantly inhibited (80%) the lytic capability of such cytotoxic T-cells generated from "one-way human MLR" cultures.

TABLE 2

Inhibitory Effect of HE-33 on One-way MLR-generated Human T-lymphocyte-mediated Cytolysis

| Type of Treatment | % Specific Lysis E:T 25:1 | % Inhibition |
|---|---|---|
| Sensitized T-cells only | 20 | — |
| Non-sensitized T-cells only | 1 | — |
| Sensitized T-cells + CsA (100 μM) | 2 | 90 |
| Sensitized T-cells + HB-33 (100 μM) | 4 | 80 |

Table 3 shows essentially the same results as Table 2 except that these experiments were conducted in mice (ex vivo). H-2-restricted cytotoxic T-cells were generated in vivo in the presence or absence of HE-33. As can be seen in the table, when 100 mg/kg of HE-33 was administered i.v. every three days, it induced a 92% inhibition of $H-2^K$ anti-$H-2^d$-specific cytotoxic T-cell activity. Although oral administration of HE-33 (400 mg/kg) was not as effective as the i.v. route, some inhibitory effect (32%) was also observed.

TABLE 3

Effect of Administration of HE-33 in vivo on the Generation of $H-2^K$ Anti-$H-2^d$ CytotoxicT-Cell Activity*

| Ratio | Control % Lysis | I.V. Injected % Lysis | Oral Fed % Lysis |
|---|---|---|---|
| 25:1 | 8 | 1 | 5 |
| 12.5:1 | 4 | 0 | 2 |
| 6.25:1 | 2 | 0 | 2 |
| 3.12:1 | 1 | 0 | 1 |
| L.U. | 13 | 1 | 9 |
| % Inhibition: | | 92% | 32% |

*$C_3H/J$ mouse was injected with $2 \times 10^7$ DBA/2 spleen cells for 9 days. HE-33 was administered either orally (400 mg/kg) or intravenously (100 mg/kg) on day 0 and every three days. Con-A stimulated DBA/2 spleen cells were used as target cells.

Table 4 is representative of results from three experiments demonstrating the inhibitory effect of HE-33 on IL-2 and IL-4, which are T-cell cytokines known to be involved in the early phase of rejection (10).

TABLE 4

Effects of HE-33 (100 μM) on Production of IL-2, IL-4, IL-10 and Interferon-gamma Production in PHA-stimulated Cultures of Human PBMC

| Cytokine | Duration | PHA pg/mL | PHA + HE-33 pg/mL | % Inhibition | PHA + CsA pg/mL | % Inhibition | PHA + Fk506 pg/mL | % Inhibition |
|---|---|---|---|---|---|---|---|---|
| IL-2 | 24 hours | 409 | 418 | 0 | 179 | 57 | 0.7 | 100 |
|  | 48 hours | 616 | 148 | 76 | 98 | 84 | 16 | 97 |
|  | 72 hours | 166 | 51 | 70 | 56 | 66 | 16 | 91 |
|  | 96 hours | 19 | 48 | 0 | 52 | 0 | 23 | 0 |
| IL-4 | 24 hours | 692 | 1041 | 0 | 73 | 90 | 18 | 98 |
|  | 48 hours | 1483 | 193 | 87 | 105 | 93 | 17 | 99 |
|  | 72 hours | 1156 | 860 | 26 | 96 | 92 | 10 | 99 |
|  | 96 hours | 135 | 101 | 25 | 20 | 86 | 10 | 93 |
| IL-10 | 24 hours | 559 | 441 | 21 | 94 | 83 | 173 | 69 |
|  | 48 hours | 1004 | 1304 | 0 | 427 | 58 | 235 | 77 |
|  | 72 hours | 578 | 790 | 0 | 579 | 0 | 228 | 61 |
|  | 96 hours | 834 | 991 | 0 | 444 | 47 | 200 | 76 |
| IFN-γ | 24 hours | 625 | 980 | 0 | 165 | 74 | 0 | 100 |
|  | 48 hours | 6736 | 6146 | 9 | 7159 | 0 | 155 | 98 |
|  | 72 hours | 2886 | 5390 | 0 | 7054 | 0 | 232 | 92 |
|  | 96 hours | 5459 | 6105 | 0 | 3817 | 30 | 225 | 96 |

Table 5 shows the inhibitory effect of HE-33 on tetanus toxoid-specific T-cell proliferation. Tissue rejection is an antigen-specific immune process which involves antigen-specific T-cell proliferation in the early phase of the immune response. The secondary immune response of an individual who had been immunized and boosted against a specific antigen, tetanus, was 91% inhibited by HE-33.

TABLE 5

Inhibitory Effect of HE-33 on Antigen-Specific Proliferation

| Type of Treatment | Proliferation (CPM) | % Inhibition |
|---|---|---|
| Medium | 42 | — |
| TTX | 1034 | — |
| TTX + HE-33 (10 μg/mL) | 94 | 91% |

TABLE 5-continued

Inhibitory Effect of HE-33 on Antigen-Specific Proliferation

| Type of Treatment | Proliferation (CPM) | % Inhibition |
|---|---|---|
| TTX + HE-33 (1 μg/mL) | 358 | 65% |
| TTX + CsA (100 μM) | 79 | 92% |
| TTX + CsA (10 μM) | 238 | 77% |

Table 6 is the result of experiments performed with the mouse monoclonal antibody, OKT3/antiCD3. Currently, it is the only monoclonal antibody licensed for use in clinical organ transplantation. The antibody is directed against the human CD3 antigen on all T-cells. In vitro, anti-CD3 is a polyclonal activator but in vivo, anti-CD3 either acts as a lytic antibody, activating the complement system to eliminate T-cells or opsonizes T-cells for phagocytosis. The in vitro results with anti-CD3 shown in Table 6 indicated that HE-33 induced 97% inhibition of the anti-CD3-induced polyclonal activation of the T-cells within the PBMC population suggesting that the cellular target for HE-33 is the T-cell.

TABLE 6

Inhibitory Effect of HE-33 on Anti-CD3-induced T-cell Proliferation

| Type of Treatment (2 × 10⁵ cells/well) | Proliferation (CPM) | % Inhibition |
|---|---|---|
| Anti-CD3 only | 1272 | — |
| Anti-CD3 + HE-33 (10 μM) | 289 | 77% |
| Anti-CD3 + HB-33 (100 μM) | 43 | 97% |
| Anti-CD3 + CsA (100 μM) | 62 | 95% |

Anti-CD3 mAb was used at 1 ng/mL concentration.

Table 7 represents the result of an experiment showing that HE-33 inhibited the calcium-dependent protein kinase-C (PK-C)-mediated cell proliferation. CsA is known to function via the calcium/calmodulin pathway (Abbas et al.). Thus, CsA was used in this experiment as a positive control. As can be seen in the table, CsA inhibited this pathway 96% as well as HE-33 or 1–24 (97% and 98% respectively). Interestingly, the conventional cell permeable cAMP compound, dbcAMP, inhibited this pathway by only 38%. This suggested that HE-33/I–24 are derivatives of cAMP which differ significantly from conventional cAMPs.

TABLE 7

Inhibitory Effect of HE-33 on Protein Kinase-C-Mediated T-cell Proliferation

| Stimulation | Proliferation (CPM) | % Inhibition |
|---|---|---|
| PMA + A23187 only | 1024 | — |
| PMA + A23187 + HE-33 (100 μM) | 31 | 97% |
| PMA + A23187 + I-124 (100 μM) | 16 | 98% |
| PMA + A23187 + dbcAMP (100 μM) | 645 | 38% |
| PMA + A23187 + CsA (100 μM) | 46 | 96% |
| PMA + A23187 + Forskolin (100 μM) | 476 | 55% |

PMA (1.25 ng/mL)
A23187 (0.25 μM)

Table 8 is the result of a toxicology study. All mice survived for the duration of the study. Drug-related clinical signs of toxicity occurred between 10 minutes and 5 hrs. after dosing on Day 1. Animals in the 150–400 mg HE-33/kg dose groups showed signs of hypoactivity, flattened posture with or without closed eyes and slow breathing, suggestive of central nervous system activity. After Day 1, however, all mice in saline and drug-treated groups were normal between Days 2 and 8. The no-effect-level (NOEL) for single IV administration of HE-33 in mice was 100 mg/kg, whereas the maximum tolerated dose (MTD) was greater than or equal to 400 mg/kg.

TABLE 8

Single Dose Range-Finding Study of Test Article HE-33 in Mice
Clinical Observations for Animals Treated with Test Article HE-33 or Saline

| Animal ID (dose) | Clinical Observations on Study Day | | | | | | | | | | |
|---|---|---|---|---|---|---|---|---|---|---|---|
| | 1 | | | | | | | | | | |
| Clinical Observations | 10 min | 30 min | 60 min | 5 hr. | 2 | 3 | 4 | 5 | 6 | 7 | 8 |
| 6 (0 mg/kg)[a] | | | | | | | | | | | |
| Normal | x[b] | x | x | x | x | x | x | x | x | x | x |
| 7 (0 mg/kg)[a] | | | | | | | | | | | |
| Normal | x | x | x | x | x | x | x | x | x | x | x |
| 1 (1.5 mg/kg) | | | | | | | | | | | |
| Normal | x | x | x | x | x | x | x | x | x | x | x |
| 2 (15 mg/kg) | | | | | | | | | | | |
| Normal | x | x | x | x | x | x | x | x | x | x | x |
| 3 (75 mg/kg) | | | | | | | | | | | |
| Normal | — | x | x | x | x | x | x | x | x | x | x |
| Vocalization | x[c] | — | — | — | — | — | — | — | — | — | — |
| 8 (100 mg/kg) | | | | | | | | | | | |
| Normal | x | x | x | x | x | x | x | x | x | x | x |
| 4 (150 mg/kg) | | | | | | | | | | | |

TABLE 8-continued

Single Dose Range-Finding Study of Test Article HE-33 in Mice
Clinical Observations for Animals Treated with Test Article HE-33 or Saline

| Animal ID (dose) Clinical Observations | Clinical Observations on Study Day | | | | | | | | | | |
|---|---|---|---|---|---|---|---|---|---|---|---|
| | 1 | | | | | | | | | | |
| | 10 min | 30 min | 60 min | 5 hr. | 2 | 3 | 4 | 5 | 6 | 7 | 8 |
| Normal | — | — | — | x | x | x | x | x | x | x | x |
| Slow breathing | x | x | x | — | — | — | — | — | — | — | — |
| Hypoactive FPSR[d] | x | x | x | — | — | — | — | — | — | — | — |
| 9 (200 mg/kg) | | | | | | | | | | | |
| Normal | x | x | x | x | x | x | x | x | x | x | x |
| 10 (200 mg/kg) | | | | | | | | | | | |
| Normal | x | x | x | x | x | x | x | x | x | x | x |
| 5 (300 mg/kg) | | | | | | | | | | | |
| Normal | — | — | — | — | x | x | x | x | x | x | x |
| Slow breathing | x | x | x | x | — | — | — | — | — | — | — |
| | — | — | — | x | — | — | — | — | — | — | — |
| Cool to touch | x | x | x | x | — | — | — | — | — | — | — |
| Hypoactivity FPSR[d] | x | x | x | — | — | — | — | — | — | — | — |
| 11 (300 mg/kg) | | | | | | | | | | | |
| Normal | x | — | — | x | x | x | x | x | x | x | x |
| Slow breathing | — | x | x | — | — | — | — | — | — | — | — |
| | — | x | x | — | — | — | — | — | — | — | — |
| Hypoactivity FPSR[d] | — | x | x | — | — | — | — | — | — | — | — |
| 12 (400 mg/kg) | | | | | | | | | | | |
| Normal | x | — | — | — | x | x | x | x | x | x | x |
| Slow breathing | — | — | — | x | — | — | — | — | — | — | — |
| | — | x[c] | x | x | — | — | — | — | — | — | — |
| FPSR[d] | | | | | | | | | | | |

[a]Animals were dosed with saline adjusted to pH 8.55.
[b]Observations are recorded as present (x) or not observed (—).
[c]Additional observation was reported in the time interval closest to when it occurred.
[d]FPSR = Flattened posture with or without closed eyes; animal would periodically have a startled response in response to or without a noise stimulus.

Effect of HE-33 on Skin-Grafting

In order to demonstrate the immunosuppressive activity of HE-33 in vivo, tail skin from Balb/C mice was grafted onto C57BL/6 mice. Balb/C and C57BL/6 mice are genetically histoincompatible in that Balb/C is of haplotype H-$2^d$ whereas C57BL/6 is of haplotype H-$2^b$. The surgical procedure used in these experiments was performed according to the procedures reported by Matriano, J. E. et al. (J. Immunol., 1996, 156:4114–4119).

As shown in Table 9, Groups 2 and 3 were given HE-33 by I.V. injection everyday from 2 days prior to grafting. Mice in groups 4 and 5 were orally administered HE-33 daily from 2 days prior to grafting. Rejection was assessed by observing redness and dryness of the graft (Natriano, J. E. et al., J. Immunol., 1996, 153:1505–1514). At a dose of 100 mg/kg I.V., HE-33 prolonged graft survival by approximately 4 days.

TABLE 9

Effect of HE-33 on Skin Graft Survival in Mice

| Group No. | Type of Treatment | Skin Graft Survival (Days) | Mean Survival Time (Days) |
|---|---|---|---|
| 1 | No Drug | 8, 9, 9, 9, 11 | 9.2 |
| 2 | 50 mg/kg (I.V.) | 9, 10, 11, 11 | 10.25 |
| 3 | 100 mg/kg (I.V.) | 11, 12, 14, 15, 15 | 13.4 |
| 4 | 200 mg/kg (oral) | 8, 9, 9, 10, 10 | 9.2 |
| 5 | 400 mg/kg (oral) | 9, 9, 10, 10, 11 | 9.8 |

C57BL/6 mice were grafted with tail skin from Balb/c mice. Drug treatment was started two days prior to grafting. Casts were removed on day 6 and survival of the graft was scored everyday. Rejection was defined on change in thickness, dryness and >80% redness of the graft.

Prevention of GVHD

Prevention or suppression of GVHD in recipient mice was achieved by treating donor mice prior to transplantation with a therapeutically effective amount of HE-33 a sufficient amount of time before transfer of donor cells to recipient $(B_6 \times C_3H)F_1$ mice. A preferred time of treating the donor is about 24 hours before transfer of cells, tissues, or organs from donor to recipient, although prevention or suppression of GVHD can be achieved using the method of the invention by treating the donor from about one hour to about 48 hours before transfer of cells, tissue or organs from donor to recipient.

Figure 2:
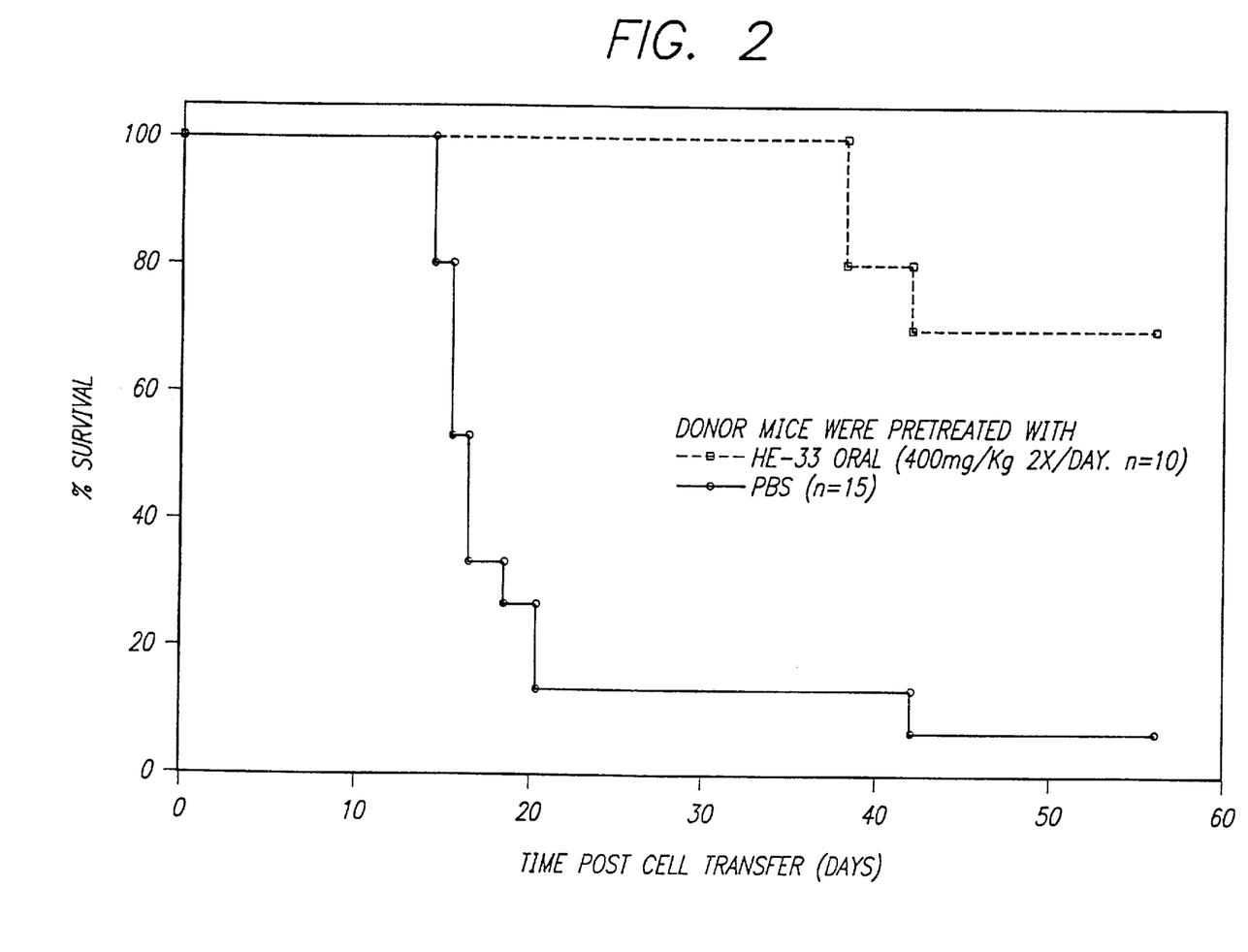
FIG. 2 shows the immunosuppressive effects of treating donor animals with HE-33 on GVHD in recipients.

Table 10 depicts the ex-vivo results on the NK activity of transferred cells. Oral pretreatment of donor mice for 24 hours with 400 mg/kg HE-33 (Bid) resulted in close to 80% elimination/suppression of endogenous NK cell activity as compared to about 35% for i.v. treatment of donor mice. As shown in FIG. 2, this suppression of endogenous NK cell activity resulted in prevention of GVHD in recipients of the NE-suppressed cell population.

FIG. 2 is representative of results from one experiment showing the dramatic inhibitory effect of HE-33 on GVHD in $(B_6 \times C_3H)F_1$ mice that received cells from HE-33 pretreated C57BL/6 donor mice. By 55 days post cell transfer, more than 95% of recipients of cells from saline-pretreated donor mice had died as compared to only 30% of recipients of cells from HE-33-pretreated mice. Moreover, by day 30, post cell transfer, 90% of recipients of cells from saline-treated mice had died whereas none of the recipients of cells from HE-33-treated cells had died (P<0.0000001). The mean survival time (MST) of the mice that died was 13 days for control mice and 46 days for mice that received HE-33-pretreated cells.

Figure 3:
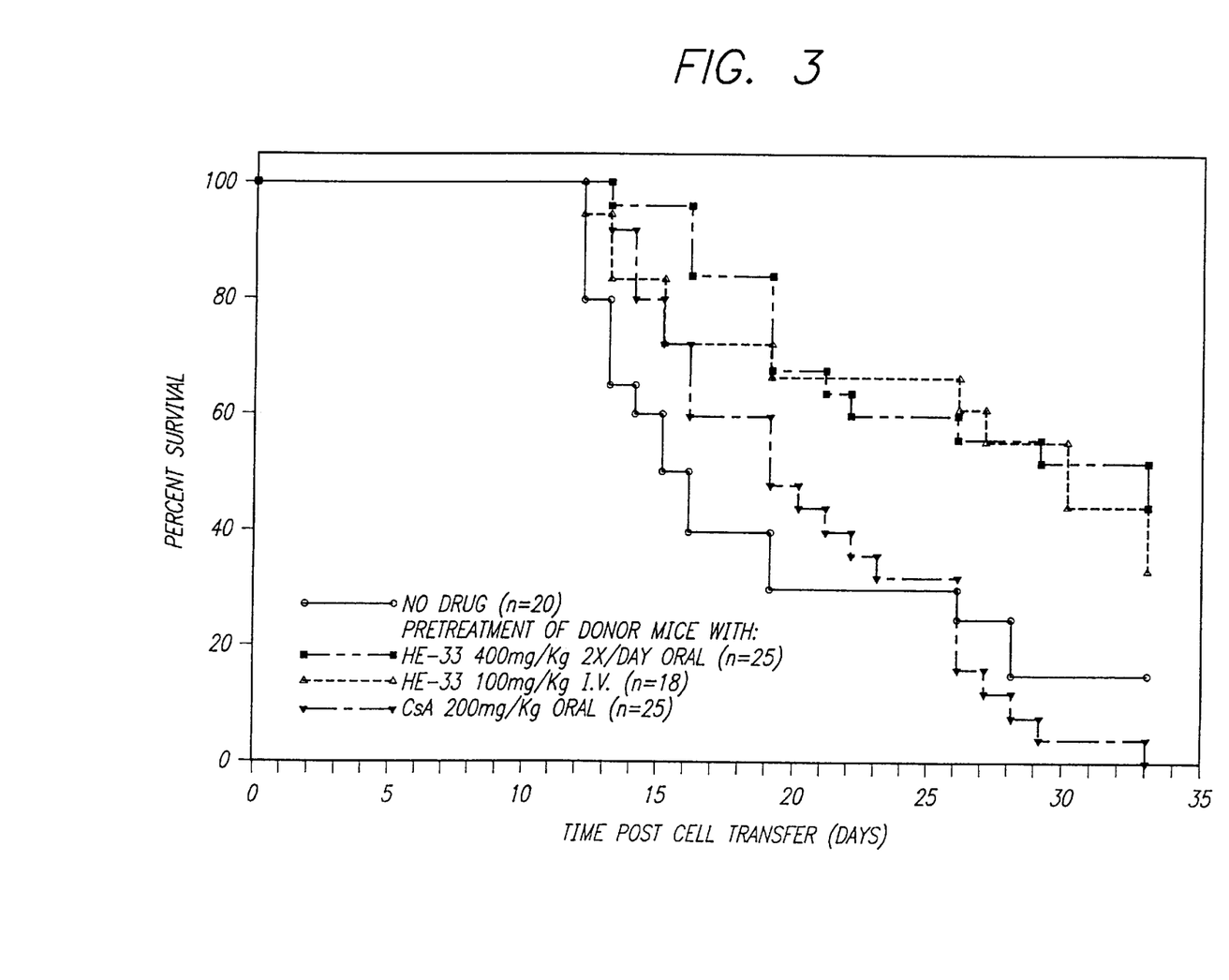
FIG. 3 shows the immunosuppressive effects of treating donor animals with either HE-33 or cyclosporin on GVHD in recipients.

FIG. 3 depicts the results of a second experiment in which the effect of HE-33 on GVHD was compared with that of cyclosporin-A (CsA). On day 33 post cell transfer, 100% (25/25) of the $(B_6 \times C_3H)F_1$ mice that received cells from CsA-pretreated C57BL/6 mice had died as compared with 50% (11/25) of the $(B_6 \times C_3H)F_1$ mice that received cells from HE-33-pretreated C57BL/6 mice. These results clearly demonstrate the efficacy of HE-33 in preventing GVHD. Both the oral and intravenous routes of administration of HE-33 were effective in preventing GVHD. However, the oral route was better than the i.v. route.

TABLE 10

Pretreatment of C57BL/6 mice with HE-33 via different routes of administration (Donors of cells to (C57BL/6 × C3H/j)F1 mice for GVHD induction) NK Cell Activity using YAC-I Cells as Target

| Serial # | Type of Treatment/Day | Type of Cells | Effector/ Target Ratio | Percent Lysis | Percent Suppression |
|---|---|---|---|---|---|
| 1 | 100 mg/kg HE-33 (IV) | Spleen | 100:1 | 14% | 33% |
| 2 | 400 mg/kg (Bid) HE-33 (oral) | Spleen | 100:1 | 5% | 76% |
| 3 | PBS oral + IV | Spleen | 100:1 | 21% | — |

What is claimed is:

1. A method for suppressing graft-versus-host reaction in a transplant recipient which method comprises administering to a donor prior to transplantation a pharmaceutical composition comprising a therapeutically effective amount of a composition comprising a compound or agonist having one of the following structures:

wherein
$R_1$, $R_2$ are same or different or in any independent combination of $R_1$=H, —$(CH_2)_n$ OH where n=1–5; $C_{1-12}$ alkyl, substituted or unsubstituted, straight chain or branched, with 0–6 double bonds;
$R_3$, $R_4$, $R_5$ are the same or different or may be selected in any independent combination of H, Cl, Br, F, I, $NH_2$, $NHR_1$, $N(R_1)_2$, OH, $OR_1$, SH, and $SR_1$, and
$R_6$=H, $NH_4^+$, $Na^+$ and any other physiologically acceptable cation; or
R6=a primary, a secondary, or a tertiary ammonium ion wherein the alkyl substituent(s) are independently selected from the group consisting of linear or branched $c_{1-6}$ alkyls.

2. The method of claim 1 wherein said compound or agonist thereof is in association with a pharmaceutical carrier or diluent.

3. The method of claim 1 which comprises administering to said donor a therapeutically effective amount of the compound of formula I wherein $R_1$=$R_2$=n-propyl; $R_3$=$R_4$=H; $R_5$=OH; and $R_6$=$Na^+$.

4. The method of claim 1 which comprises administering to said donor a therapeutically effective amount of the compound of formula I wherein $R_1$=$R_2$=n-butyl; $R_3$=$R_4$=H; $R_5$=OH; $R_6$=$NH_4^+$.

* * * * *